United States Patent [19]

Toida et al.

[11] 4,309,411
[45] Jan. 5, 1982

[54] SKIN CLEANSING PREPARATION

[75] Inventors: Hiroshi Toida, Tokyo; Masumi Koishi, Sagamihara, both of Japan

[73] Assignee: Kabushiki Kaisha Kishohin Kagaku Kaiho Kenkyusho, Tokyo, Japan

[21] Appl. No.: 113,803

[22] Filed: Jan. 21, 1980

[30] Foreign Application Priority Data

Mar. 23, 1979 [JP] Japan .................................. 54/34775

[51] Int. Cl.³ ........................ A61K 7/021; A61K 7/48
[52] U.S. Cl. ........................................ 424/63; 424/78; 424/80; 424/263; 424/273 R; 424/345; 424/357; 424/361; 424/362; 424/363; 424/365; 424/366; 424/319
[58] Field of Search ................................, 424/63, 365

[56] References Cited

U.S. PATENT DOCUMENTS 4,087,555 5/1978 Barnett et al. ...................... 424/365

FOREIGN PATENT DOCUMENTS

| 2107429 | 9/1971 | Fed. Rep. of Germany | 424/63 |
| 2352266 | 4/1975 | Fed. Rep. of Germany | 424/63 |
| 1493579 | 7/1967 | France | 424/63 |
| 2034415 | 2/1970 | France | 424/59 |

OTHER PUBLICATIONS

Sagarin Cos. Sci. and Technology, 1975, pp. 18 to 26.

Primary Examiner—Dale R. Ore
Attorney, Agent, or Firm—James E. Nilles

[57] ABSTRACT

A pack cosmetic which comprises a mixture of (a) a solution of a water-soluble polymer and (b) particles of a water-insoluble polymeric compound having adhered thereon an inorganic pigment.

13 Claims, 2 Drawing Figures

SKIN CLEANSING PREPARATION

BACKGROUND OF THE INVENTION

1. Field of the Invention

The present invention relates to a pack cosmetic comprising a mixture of (a) a solution of a water-soluble polymer and (b) particles of a water-insoluble polymeric compound having adhered thereto a powdery inorganic pigment.

2. Description of the Prior Art

In conventional pack cosmetics comprising polyvinyl alcohol as a base, there are incorporated vitamins, hormones, anti-inflammatory agents and polyhydric alcohols such as glycerin, propylene glycol or 1,3-butylene glycol as humectants. Furthermore, inorganic pigments are incorporated according to the intended uses.

It is known that such inorganic pigment-incorporated pack cosmetics are superior to inorganic pigment-free pack cosmetics, with respect to the capacity of removing dirt from the skin.

Inorganic pigments ordinarily have hydrophilic surfaces. Thus, when these are incorporated into pack cosmetics, although the resulting cosmetics are excellent in capacity of absorbing hydrophilic dirts from the surface of the skin, they are inferior in capacity of absorbing excessive oleophilic dirts.

A need therefore continues to exist for a pack cosmetic which is capable of absorbing both hydrophilic and oleophilic dirts from the skin.

SUMMARY OF THE INVENTION

It is therefore an object of the invention to provide a pack cosmetic or skin cleansing composition.

Another object of the invention is to provide a pack cosmetic with superior capacity of absorbing oleophilic and hydrophilic dirts from the skin.

These and other objects of the invention which will become more readily apparent hereinafter, have been attained by providing a pack cosmetic which comprises a mixture of (a) a solution of a water-soluble polymer; and (b) particles of a water-insoluble polymeric compound having adhered thereon an inorganic pigment.

BRIEF DESCRIPTION OF THE DRAWINGS

The objects and features of the present invention will be apparent from the following detailed description when made in reference to the accompanying drawings, wherein.

DETAILED DESCRIPTION OF THE PREFERRED EMBODIMENTS

It was noted that the lack of adsorbance of oleophilic dirt of the pack cosmetics of the prior art could be eliminated by using particles of a polymeric compound having oleophilic surfaces in combination with an inorganic pigment adhered thereon. As a result of this discovery, a pack cosmetic capable of absorbing oleophilic dirt as well as hydrophilic dirt has been developed.

More specifically, in accordance with the present invention, by incorporating into a solution of a water-soluble polymer particle, a water-insoluble polymeric compound, having adhered thereto an inorganic pigment, the characteristic properties of both the inorganic pigment and the water-insoluble polymeric compound can be sufficiently exerted.

As the water-insoluble polymeric compound, there may be used polyamides, nylon 12, polystyrene, polyethylene, Teflon[R], Derlin[R], benzoguanamine resins and vinyl chloride resins in the form of porous or non-porous, spherical or amorphous particles having a size of about 1–1000μ.

As the inorganic pigment, there may be used for example, titanium dioxide, calcium carbonate, talc, clay, kaolin, graphite, carbon black, "high-area" or "colloidal" silica, bentonite, alumina, magnesium hydroxide and magnesium carbonate in the form of particles having a size of about 0.01 to about 100μ. Single or multi-compound pigments may be used.

As the water-soluble polymer, any of the well-known prior art water-soluble polymers used in pack cosmetics may be used. Useful water-soluble polymeric materials are water-soluble high molecular materials such as polyvinyl alcohol, polyvinylpyrrolidone, sodium alginate potassium alginate, alginic propylenglykol, sodium polyacrylic acid, xanthonegum, carboxymethylcellulose, and sodium carboxymethylcellulose.

The conventional pack cosmetics having water-soluble polymeric materials are disclosed in the literature "Manufacturing Method, Nature and Application of Microcapsule" written by T. Kondo and N. Koishi and published on Oct. 5, 1977 by Sankyo Shuppan Kabushiki Kaisha.

Figure 1:
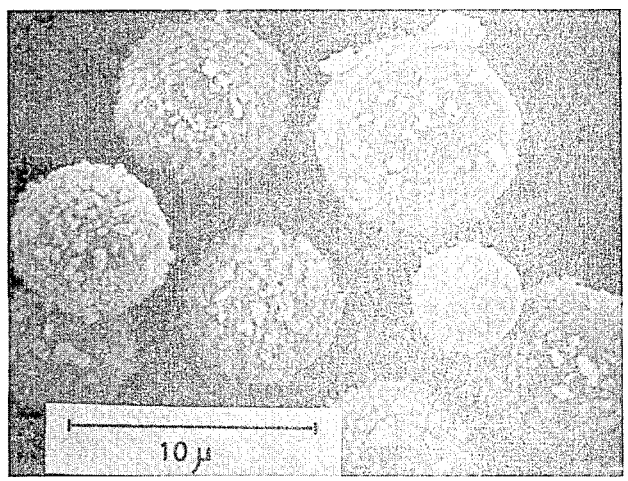
FIG. 1 is a scanning electron microphotograph illustrating titanium dioxide particles adhered to each surface of spherical nylon 12 particles at a nylon 12/titanium dioxide weight ratio of 7/1.
Figure 2:
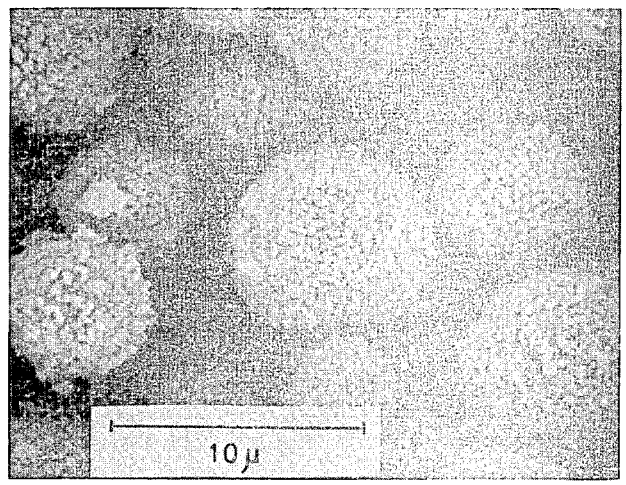
FIG. 2 is a scanning electron microphotograph illustrating the particles of FIG. 1 at a nylon 12/titanium dioxide weight of 2/1.

In order to adhere the inorganic pigment to the water-insoluble polymer, a method such as the one described as follows for nylon 12 can be used. Particles of nylon 12 are mixed with titanium dioxide in a mixer such as a ball mill, mortar or crushing mixer. Nylon 12 particles are not pulverized by this treatment, but titanium dioxide is adhered to the surface of the particles of nylon 12. At this treatment, friction is caused among the particles of nylon 12 or among the particles of nylon 12 and particles of titanium dioxide. The particles of nylon 12 are electrically charged by a frictional charging effect. By this frictional charge and the adhesive effect of a minor amount of free water adsorbed on the surfaces of nylon 12 particles from the moisture in air, hydrophilic titanium dioxide is adhered on the surfaces of nylon 12 particles in the form of single particles or aggregates, as shown in FIGS. 1 and 2, which particles are known as inorganic pigment-modified particles of a water-insoluble polymeric compound.

The ratio of the inorganic pigment to the particles of the polymeric compound can optionally be changed and controlled by changing the mixing ratio of the inorganic pigment to the particles of the polymeric compound. The ratio of inorganic pigment to polymeric particles is 0.01:1 to 1:1 preferably 0.1:1.

By the above-mentioned operation, hydrophilic and oleophilic portions are formed on the surface of the particles.

Hydrophilic dirts as well as oleophilic dirts can then be adsorbed on respective single particles.

The ratio of water-soluble polymer to pigment-covered water-insoluble polymer is 1:0.01 to 1:0.5, preferably 1:0.3.

According to the present invention, the desired degree of hydrophilicity of products can be made by a variant weight ratio of water-insoluble particles to inorganic pigment.

Accordingly, if particles of a water-insoluble polymeric compound to which an inorganic pigment is thus adhered, are incorporated into an aqueous solution of a water-soluble polymer according to the present invention, there can be obtained a pack cosmetic which is superior over the conventional pack cosmetics formed by incorporating an inorganic pigment alone. These superior effects are obtained with respect to the effects of removing dirts from the skin surface. The product has valuable sanitary and beauty effects on the skin.

The present invention will now be described in detail by reference to the following specific examples, which are not intended to limit the scope of the invention. All of "%" are percentage by weight in the following examples.

EXAMPLE 1

| | |
|---|---|
| Polyvinyl alcohol | 12.0% |
| Nylon 12 | 3.0% |
| Titanium dioxide (Rutile type) | 0.3% |
| Glycerin | 4.0% |
| Methyl p-hydroxybenzoate | 0.1% |
| Perfume | 0.1% |
| Polyoxyethylene-sorbitan monolaurate (20 ethylene oxide units) | 1.0% |
| Water | 79.5% |

A beaker having an appropriate capacity was charged with polyvinyl alcohol, glycerin, methyl p-hydroxybenzoate and water, and the temperature was elevated to 60° to 80° C. and the mixture was agitated to form a solution. A mixture obtained by mixing nylon 12 powder with titanium dioxide sufficiently for 30 minutes by an automatic ceramic mortar the perfume and polyoxyethylenesorbitan monolaurate were added to the solution under agitation. The mixture was cooled under agitation to form a skin treating composition.

EXAMPLE 2

| | |
|---|---|
| Polyvinyl alcohol | 12.0% |
| Nylon 12 | 5.0% |
| Titanium dioxide (Rutile type) | 0.2% |
| Talc | 0.3% |
| Glycerin | 5.0% |
| Methyl p-hydroxybenzoate | 0.1% |
| Dipotassium glycyrrhizate | 0.1% |
| Vitamin B$_6$ | 0.1% |
| Water | 77.2% |

A beaker having an appropriate capacity was charged with polyvinyl alcohol, glycerin, methyl p-hydroxybenzoate, dipotassium glycyrrhizate, vitamin B$_6$ and water, and the temperature was elevated to 60° to 80° C. and the mixture was agitated to form a solution. A mixture formed by mixing nylon 12 powder, titanium dioxide and talc in an automatic ceramic mortar for 30 minutes was added to the solution. The mixture was cooled under agitation to form a skin treating composition.

EXAMPLE 3

| | |
|---|---|
| Polyvinyl alcohol | 14.0% |
| Polystyrene | 3.0% |
| Talc | 0.2% |
| 1,3-Butylene glycol | 5.0% |
| Methyl p-hydroxybenzoate | 0.1% |
| Estradiol | 0.001% |
| Water | 77.699% |

A beaker having an appropriate capacity was charged with polyvinyl alcohol, 1,3-butylene glycol, methyl p-hydroxybenzoate, estradiol and water, and the temperature was elevated to 60° to 80° C. and the mixture was agitated to form a solution. A mixture formed by mixing polystyrene and talc in an automatic ceramic mortar for 30 minutes was added to the solution and the mixture was cooled under agitation to form a skin treating composition.

EXAMPLE 4

| | |
|---|---|
| Polyvinyl alcohol | 13.0% |
| Nylon 12 | 4.0% |
| Calcium carbonate | 0.2% |
| Kaolin | 0.2% |
| 1,3-Butylene glycol | 5.0% |
| Methyl p-hydroxybenzoate | 0.1% |
| Ethanol | 6.0% |
| Alkyldiaminoethylglycine hydrochloride | 0.2% |
| Allantoin | 0.1% |
| Water | 71.2% |

A beaker having an appropriate capacity was charged with polyvinyl alcohol, 1,3-butylene glycol, methyl p-hydroxybenzoate, ethanol, alkyldiaminoethylglycine hydrochloride solution, allantoin and water, and the temperature was elevated to 60° to 80° C. and the mixture was agitated to form a solution. A mixture formed by mixing nylon 12 powder, calcium carbonate and kaolin in a ball mill for 30 minutes was added to the solution, and the mixture was cooled under agitation to form a skin treating composition.

What is claimed as new and desired to be secured by Letters Patent of the United States is:

1. A method of preparing a cleansing cosmetic preparation which is capable of absorbing both hydrophilic and oleophilic dirts from the skin, which consists essentially of:
   (a) first mixing by agitation particles of a water-insoluble polymer and particles of an inorganic pigment until the inorganic pigment particles are adhered to the surface of the water-insoluble polymer particles, the weight ratio of inorganic pigment particles to polymeric particles being from 0.01:1 to 1:1; and
   (b) then incorporating the water-insoluble polymer particles with the inorganic pigment particles adhered thereto into a previously prepared aqueous solution of a water-soluble polymer, the weight ratio of water-soluble polymer to pigment-coated water-insoluble polymer being from 1:0.01 to 1:0.5.

2. The method according to claim 1, wherein said inorganic pigment particles have a size in the range of about 0.01 to 100 microns.

3. The method according to claim 1, wherein said water-insoluble polymer particles have a size in the range of about 1 to 1000 microns.

4. The method according to claim 1, wherein said inorganic pigment is selected from the group consisting of titanium dioxide, calcium carbonate, talc, clay, kaolin, graphite, carbon black, silica, bentonite, alumina, magnesium hydroxide, and magnesium carbonate.

5. The method according to claim 4, wherein said water-insoluble polymer is selected from the group consisting of polyamide, nylon 12, polystyrene, polyethylene, benzoquanamine resin, and vinyl chloride resin.

6. A method of preparing a cleansing cosmetic preparation which is capable of absorbing both hydrophilic and oleophilic dirts from the skin, which consists essentially of:
   (a) first mixing by agitation particles of a water-insoluble polymer and particles of an inorganic pigment until the inorganic pigment particles are adhered to the surface of the water-insoluble polymer particles, and
   (b) then incorporating the water insoluble polymer particles with the inorganic pigment particles adhered thereto into an aqueous solution of a water-soluble polymer, wherein said inorganic pigment particles have a size in the range of about 0.01 to 100 microns, said water-insoluble polymer particles have a size in the range of 1 to 1000 microns, the weight ratio of said water-soluble polymer to said water-insoluble polymer particles with said inorganic pigment particles adhered thereto is in the range of 1:0.01 to 1:0.5, the weight ratio of said inorganic pigment to said water-insoluble polymer is in the range of 0.01:1 to 1:1, said inorganic pigment is selected from the group consisting of titanium dioxide, calcium carbonate, talc, clay, kaolin, graphite, carbon black, silica, bentonite, alumina, magnesium hydroxide, and magnesium carbonate, and said water-insoluble polymer is selected from the group consisting of polyamide, nylon 12, polystyrene, polyethylene, benzoquanamine resin, and vinyl chloride resin.

7. A cleansing cosmetic preparation which is capable of removing both hydrophilic and oleophilic dirts from the skin made by the method of claim 2.

8. A cleansing cosmetic preparation which is capable of removing both hydrophilic and oleophilic dirts from the skin made by the method of claim 3.

9. A cleansing cosmetic preparation which is capable of removing both hydrophilic and oleophilic dirts from the skin made by the method of claim 4.

10. A cleansing cosmetic preparation which is capable of removing both hydrophilic and oleophilic dirts from the skin made by the method of claim 5.

11. A cleansing cosmetic preparation which is capable of removing both hydrophilic and oleophilic dirts from the skin made by the method of claim 6.

12. A cleansing cosmetic preparation which is capable of removing both hydrophilic and oleophilic dirts from the skin, wherein said preparation is made by
   (a) first mixing by agitation a binary mixture of particles of a water insoluble polymer and particles of an inorganic pigment until the inorganic pigment particles are adhered to the surface of the water-insoluble polymer particles; and
   (b) then incorporating the water-insoluble polymer particles with the inorganic pigment particles adhered thereto into an aqueous solution of a water-soluble polymer, wherein the weight ratio of said water soluble polymer to said water-insoluble polymeric particles with said inorganic pigment particles adhered thereto is in the range of 1:0.01 to 1:0.5 and wherein the weight ratio of said inorganic pigment to said water-insoluble polymer is in the range of 0.01:1 to 1:1.

13. The cleansing cosmetic preparation of claim 12, wherein said inorganic pigment is selected from the group consisting of titanium dioxide, calcium carbonate, talc, clay, kaolin, graphite, carbon black, silica, bentonite, alumina, magnesium hydroxide, and magnesium carbonate, and said water-insoluble polymer is selected from the group consisting of polyamide, nylon 12, polystyrene, polyethylene, benzoquanamine resin, and vinyl chloride resin.

* * * * *